United States Patent [19]

Carter et al.

[11] Patent Number: 4,632,909
[45] Date of Patent: Dec. 30, 1986

[54] MONOCLONAL ANTIBODIES WHICH BLOCK INFECTIVITY OF MALARIAL PARASITES TO MOSQUITOES

[75] Inventors: Richard Carter, Kensington; Louis H. Miller, Bethesda, both of Md.

[73] Assignee: The United States of America as represented by the Department of Health and Human Services, Washington, D.C.

[21] Appl. No.: 547,235

[22] Filed: Oct. 31, 1983

[51] Int. Cl.$^4$ .................. G01N 33/536; C12N 5/00; A61K 39/395; C12P 21/00

[52] U.S. Cl. ....................... 436/542; 435/68; 435/240; 436/548; 424/85; 935/104; 935/107; 935/110

[58] Field of Search ............... 436/548, 542; 435/68, 435/70, 172, 240, 948; 424/9, 85, 177; 260/112 R; 935/89, 104, 106–108, 110

[56] References Cited

PUBLICATIONS

Hall, R. et al., Molecular and Biochemical Parasitology, vol. 7, pp. 247–265 (1983).
Rener, J. et al., Proc. Natl. Acad. Sci., USA, vol. 77 (11), pp. 6797–6799 (1980).
Rener, J. et al., Fed. Proc., vol. 41 (3), abstract 1249 (1982).
Aikawa, M. et al., J. Protozool., vol. 28 (3), pp. 383–388 (1981).
Kaushal, D. C. et al., J. Immunol., vol. 131 (5), pp. 2557–2562 (1983).
Yoshida, N. et al., J. Exp. Med., vol. 154 (4), pp. 1255–1236 (1981).
Meuwissen, J. H., Mol. Biochem. Parasitol, Supp. 212 (1982).
Deans, J. A. et al., Clin. Exp. Immunol., vol. 49 (2), pp. 297–309 (1982).
Hall, R. et al., Mol. Biochem. Parasitol., vol. 7 (3), pp. 247–266 (1983).
Carter et al.; Nature, vol. 263, pp. 57–60 (1976).
Gwadz, Robert W.; Science, vol. 193, pp. 1150–1151 (1976).
Carter et al.; Exp. Parasitology, vol. 47, pp. 194–208 (1979).
Rener et al.; J. Exp. Med., vol. 158, pp. 976–981 (1983).
Kirk-Othmer, Enclyc. of Chem. Tech.; vol. 5, pp. 529–532 (1979).
Carter et al.; Exp. Parasit., vol. 47, pp. 185–193 (1979).
Kaushal et al.; J. Immunology (in press).

*Primary Examiner*—Blondel Hazel
*Assistant Examiner*—M. Moskowitz
*Attorney, Agent, or Firm*—John S. Roberts, Jr.

[57] ABSTRACT

Monoclonal antibodies have been developed that bind with one or more proteins located on the surface of gametes or zygotes of malaria parasites. These antibodies are specific for antigens on mosquito midgut stages of malaria parasite and sterilize the parasites in mosquitoes otherwise capable of transmitting the disease. The monoclonal antibodies are specific for the 255, 59 and 53 kilodalton surface proteins on *Plasmodium falciparum* and for the 25 kilodalton surface protein on zygotes and ookinetes of *Plasmodium gallinaceum*.

12 Claims, 2 Drawing Figures

1) BLOCK FERTILIZATION
2) BLOCK ZYGOTE DEVELOPMENT

MONOCLONAL ANTIBODIES WHICH BLOCK INFECTIVITY OF MALARIAL PARASITES TO MOSQUITOES

UTILITY

The monoclonal antibodies (MAbs) of this invention suppress or eliminate the transmission of malaria by blocking the transmission of the disease to mosquitoes. These MAbs, exhibiting affinity and specificity for proteins located on the surface of gametes or ookinetes of the malaria parasite, disrupt the sexual stage of the parasite's life cycle at two points: (a) blocking fertilization of the gametes and thus preventing formation of the zygote; and (b) blocking development of the zygote in the mosquito midgut.

Material Information Disclosure

Kirk-Othmer, *Encyclopedia of Chemical Technology*, Vol. 5, pp 529-532 (1979) provides background information on the malarias, the parasite's life cycle, and common methods of treating the disease.

Carter et al, *Experimental Parasitology*, Vol. 47, pp 194-208 (1979) discloses preliminary experiments dealing with chicken malaria and ther antibody-antigen response.

Carter et al, *Nature*, Vol. 263, pp 57-60 (1976) and Gwadz, Robert W., *Science*, Vol. 193, pp 1150-1151 (1976) both disclose preliminary experiments with chicken malaria and an eradication scheme using parasite gametes plus formalin-treated or X-irradiated infected blood.

The above three publications all disclose schemes for reducing infectivity of chicken malaria but do not use monoclonal antibody techniques or recombinant DNA technology.

Rener et al, *PNAS*, Vol. 77, pp 6797-6799 (1980) discloses the use of anti-gamete monoclonal antibodies in blocking the transmission of chicken malaria. The present invention discloses MAbs against *P. falciparum* in addition to preliminary descriptions of the gamete surface determinants involved. This article is incorporated by reference.

Rener et al, *J. of Exp. Medicine* (in press).
Kaushal et al, *J. of Exp. Medicine* (in press).

The latter two articles form the basis of the invention disclosed herein.

Statement of Deposit

The monoclonal antibodies of this invention are deposited in the American Type Culture Collection (ATCC), located at 12301 Parklawn Drive, Rockville, Md. 20852. The accession numbers are: IIC5-B10-1, #HB-8392, IA3-B8-5, #HB-8393; and IID2-C5-1, #HB-8391. The deposit in the ATCC affords permanence of the deposit in the manner prescribed by the Patent and Trademark Office and without restrictions on public access.

BACKGROUND

Figure 1:
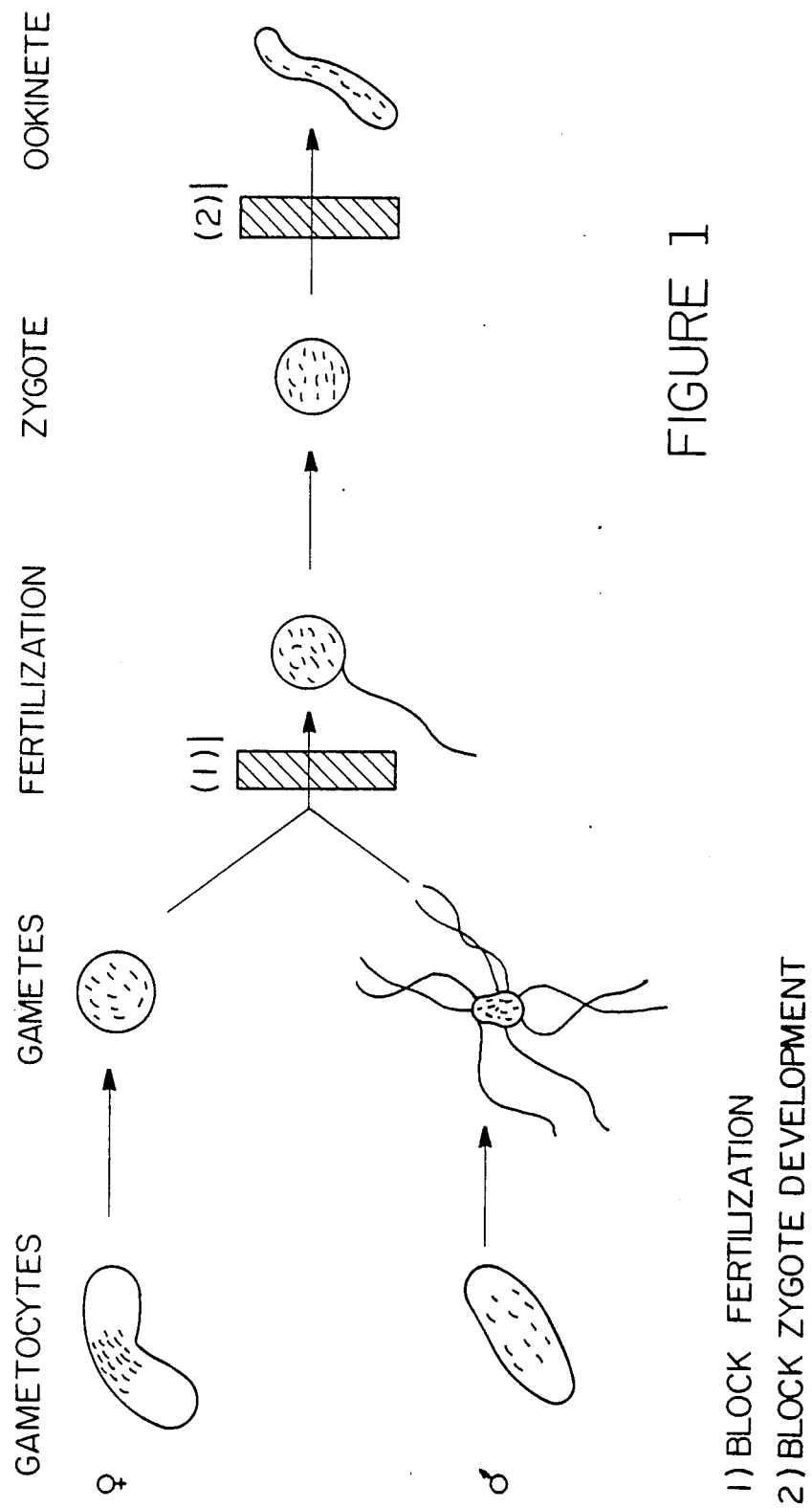
FIG. 1 is a schematic representation of the disclosed processes. The points of blocking transmission of the parasite; i.e., blocking infectivity, are labelled as numbers 1 and 2.

Malaria, once successfully controlled and virtually eradicated in many tropical regions by the use of residual insecticides, is again highly prevalent due to the development of insecticide-resistant mosquitoes as well as the logistical problems of maintaining long-term antimalaria campaigns. Today, over one billion people are at significant risk from this debilitating and often life threatening disease.

Drugs that suppress the asexual forms of the malaria parasite are commonly used to prevent or cure clinical symptoms. However, resistance of many parasite strains to antimalarial drugs poses a serious problem and it is only a question of time before such resistance renders most or all currently available categories of antimalarial drug ineffective against the parasites in many regions. Under these circumstances the development of means of immunizing against malaria provides an urgently needed alternative method of control.

Malaria is a complex of diseases caused by infection with species of the protozoan parasite Plasmodium. In man four species cause infection: *P. falciparum*, *P. vivax*, *P. ovale*, and *P. malariae*. In chickens, *P. gallinaceum* causes the disease. The normal transmission of plasmodia between individuals occurs through mosquito vectors. When an infective mosquito bites a susceptible individual, the insect inoculates sporozoites of the plasmodium into the blood stream of the new host. The sporozoites of human malaria enter cells of the liver, undergo a period of asymptomatic development of 10 days to about 2 weeks, and then re-enter the blood stream. Here the parasites multiply as intracellular parasites of the red blood cells (erythrocytes) in a synchronous process involving cyclic reinvasion of the erythrocytes. This phase of the infection is associated with the clinical disease. The cyclic multiplication of the parasites in the erythrocytes is due to asexual forms. Certain parasites, however, on entering erythrocytes develop into the sexual stages of the parasites—the male or female gametocytes.

The cycle continues when the gametocytes are ingested in a blood meal by a mosquito. Once inside the mosquito, gametocytes emerge from their host cells, undergo gametogenesis, and the extracellular gametes fertilize in the midgut during a blood meal. The fertilized gametes, called zygotes, transform over a period of 24 hours into a stage known as the ookinete, penetrate and continue their development on the outer wall of the mosquito gut, ultimately yielding infective sporozoites which the mosquito can transmit to a new host.

The present invention discloses two methods by which antibodies against extracellular forms of the parasites in the mosquito disrupt the subsequent development of the parasite in the mosquito. In one method, monoclonal antibodies against antigens on the gametes prevent fertilization and, in the presence of active complement, lead to lysis of gametes or newly fertilized zygotes, should any be formed. In the other method, monoclonal antibodies against a zygote-specific antigen prevent the development of the fertilized zygote (see FIG. 1). In both methods, then, the parasite's life cycle is disrupted and the potential mosquito vector sterilized of its malarial infection (see FIG. 1).

GENERAL DESCRIPTION

Male and female gametocytes located in red blood cells of the host are drawn into a mosquito during a blood meal when it "bites" the host. In the mosquito midgut, the gametocytes emerge from the red blood cells as male and female gametes. These gametes combine to form a zygote.

Provided that the sequence is not interrupted, the zygote will develop (still in the mosquito midgut) into an ookinete, which penetrates the wall of the mosquito gut and ultimately forms a parasite capable of transmission through the mosquito salivary glands into a new human host.

This invention discloses the disruption of this process at two critical points. In the first segment of this invention, monoclonal antibodies specific for antigens on the surface of the gametes block formation of the zygote by blocking fertilization of the gametes; the same antibodies destroy the parasites by lysis if active complement is present. In the second segment of this invention, monoclonal antibodies specific for antigens on the surface of the zygote block the subsequent development of the parasite in the mosquito midgut. Although the monoclonal antibodies in each segment of this invention are specific to different stages of the parasites' development in the mosquito midgut, they function to block malaria transmission.

The monoclonal antibodies of this invention were developed by known methods of hybridoma technology. Briefly, the monoclonal antibodies are derived by immunization of BALB/c mice with gametes, gametocytes, or ookinetes of the malaria parasite. Spleen cells of the immunized mice are fused with mouse myeloma cells. The hybrid cells are then grown, cloned, and identified as cells secreting monoclonal antibodies specific for antigens on the surface of the parasite gametes or zygotes. The antigens which are the targets of the monoclonal antibodies which block parasite infection in the mosquito are proteins of approximately 255, 59, and 53 Kilodalton on the surface of gametes of P. falciparum and a surface glycoprotein of 25 Kilodalton on zygotes of P. gallinaceum.

SPECIFIC DESCRIPTION

Inhibition of Gamete Fertilization

Monoclonal antibodies (MAbs) are produced that identify and are specific for target antigens on gametes of P. falciparum. The MAbs block infection of malaria parasites in mosquitoes by preventing fertilization of the gametes of the parasites in the mosquito midgut (FIG. 1). These MAbs are specific for a set of three proteins present on the surface of extracellular gametes of the malaria parasites. These proteins exhibit the following properties (and thus serve to define the MAbs):

(a) The approximate molecular weights of the proteins (under reducing conditions) on sodium dodecyl sulphate polyacrylamide (SDS-PAGE) are 255 K, 59 K, and 53 Kilodalton.

(b) The three gamete surface proteins in these molecular weight regions are immunoprecipitated simultaneously by each of the MAbs.

(c) The three proteins are each expressed on the surface of both male and female gametes of the malaria parasite and are also present and synthesized in the gametocytes prior to gametogenesis. This was demonstrated by biosynthetic labeling of P. falciparum gametocytes with $^{35}$S-methionine followed by immunoprecipitation with the MAbs.

(d) The epitopes on the protein antigen on the surface of the gametes which recognized by the MAbs are not detectable by immunofluorescence or immunoprecipitation in the asexual blood stage forms of the malaria parasite. These epitopes are therefore specific to the sexual stages of the parasites.

Purification of Female Gametes of P. falciparum

Female gametes of P. falciparum are prepared from cultures of the parasites grown in human red blood cells in which the majority of gametocytes are morphologically mature. The cultures are centrifuged at 1,000 g for 5 minutes and the cells resuspended in a solution which stimulates gametogenesis (7 mM Tris, 117 mM NaCl, 8 mM NaHCO$_3$ with 10% human serum added); the final pH of the suspension is pH 8.1. After incubating for 30 minutes at room temperature, the cells are resuspended to a 20% hematocrit and separated on a discontinuous Percoll (Pharmacia Fine Chemicals) gradient (15%, 30%, 42%, 54%, 60% Percoll in RPMI 1640 medium) by centrifuging at 16,000 g (Sorvall HB-4 swingout head) for 10 minutes.

The extracellular gametes separate in a layer at the 30%/42% interface.

Production of Monoclonal Antibodies

Mature gametocytes of P. falciparum are harvested, gametogenesis stimulated and gametes and gametocytes partially purified by density gradient centrifugation as described above. A suspension of $5 \times 10^6$ cells of this preparation in 0.5 ml of a 1:100 dilution in phosphate buffered saline (PBS), pH 7.4, of reconstituted lyophylized Bordetella pertussis (0.167 opacity units of B. pertussis equivalent to approximately $10^8$ organisms) is inoculated intraperitoneally into a BALB/c mouse. The B. pertussis is inactivated with 0.01% thimerosal and freeze-dried for storage. Three months later a similar number of gametes and gametocytes of P. falciparum are inoculated intravenously into the mouse. Three days later spleen cells from the immunized mouse are fused with myeloma cells of the line P3-NS1/1-Ag4-1(NS1) and hybrid cell lines (hybridomas) grown using standard procedures. Supernatants from the hybridoma cultures are screened by indirect immunofluorescence (IF) against air dried female gametes of P. falciparum prepared from cultures of the isolates used in immunization. Hybridoma cultures which give positive reactions are cloned by limiting dilution and screened by IF with live female gametes of P. falciparum to identify those hybridomas which secrete antibodies reacting with surface antigens on the malarial gametes. Cloned hybridomas which produce positive reactions are grown as ascites tumors in pristane primed BALB/c mice as a source of MAbs. Proteins from the ascitic fluids are precipitated with 30% ammonium sulfate and dialysed against PBS, pH 7.4.

Assay for Effect of MAbs on Infectivity of Gametocytes of P. falciparum to Mosquitoes Fresh defibrinated human blood is spun at 1,000×G for 5 minutes at room temperature and the cells washed in a solution containing 8.5 mM Tris, 140 mM NaCl, 9 mM glucose, pH 7.4 (SA solution) and resuspended to a 50% hematocrit in heat-inactivated normal human serum or in serum from freshly drawn defibrinated human blood as a source of active complement. To 150 µl samples of this suspension of uninfected erythrocytes in normal serum are added 60 µl of the appropriate MAb in the form of ascites proteins, ammonium sulfate precipitated and dialysed against PBS, pH 7.4. Mixtures of MAbs consist of 30 µl of each. The concentrations of proteins in the original solutions of MAbs in PBS are between 1 and 8 mg/ml. In samples without MAbs 60 ul of SA solution or ascitic proteins secreting unrelated antibodies are substituted. Cultured human blood containing mature gametocytes of P. falciparum is spun at 1,000×G for 5 minutes at room temperature and resuspended to a 50% hematocrit in normal human serum (inactivated at 56° C. for 30 minutes); 30 µl of this suspension is added to each mixture of MAbs and uninfected erythrocytes in human serum prepared as described above. These suspensions are immediately presented to cages of An. freeborni mosquitoes through water jacketed membrane feeders at 40° C. Mosquitoes are allowed to feed for 10 minutes and the fed mosquitoes kept at 27° C. and 60 to 70% relative humidity. Eight to nine days after feeding, the mosquitoes are dissected and their midguts examined for oocysts (products of parasite fertilization).

Biosynthetic Radiolabelling, Surface Radioiodination, Immunoprecipitation and Sodium Dodecyl Sulfatepolyacrylamide gel electrophoresis (SDS-PAGE) of Gametocytes and Female Gametes of P. falciparum.

Gametocytes of P. falciparum are biosynthetically labeled in culture with $^{35}S$-methionine and female gametes are labeled as intact cells with $^{125}I$ by the lactoperoxidase method. The labeled cells are extracted with 1% Triton X-100 and immunoprecipitated with MAbs followed by separation of SDS-PAGE.

Inhibition of Zygote Development

Monoclonal antibodies are produced which inhibit development of the fertilized zygote in mosquitoes (FIG. 1). These MAbs identify a protein antigen expressed on the surface of the zygote during transformation of the zygote to an ookinete. The antigen so defined is a surface glycoprotein of approximately 25 K on zygotes and ookinetes of P. gallinaceum (a chicken malaria parasite). This glycoprotein is expressed on the zygote surface 3 to 4 hours after fertilization of the gametes.

Purification of Zygotes and Ookinetes of P. gallinaceum

These stages are made from chicken blood parasitized with P. gallinaceum by the following methods.

Preparation of Zygotes

Zygotes (fertilized gametes) of P. gallinaceum are prepared from 5-week-old White Leghorn chickens infected with this parasite. Birds with rising parasitemias (pre-peak of infection) of 50-70% are anesthetized with ether and bled out. For each preparation, 50-60 ml of whole blood is drawn in heparinized syringes from five to six chicks and immediately diluted in 1 liter of suspended activation (SA) solution (10 mM Tris; 170 mM NaCl; 10 mM glucose, pH 7.4). The cell suspension is centrifuged at 500×g for 5 minutes and the pelleted cells resuspended to 150 ml in exflagellation solution (8 mM Tris; 150 mM NaCl; 8 mM glucose; 25 mM NaHCO$_3$ supplemented with 10% chicken serum) at a final pH for the cell suspension of 8.0-8.1. In this solution the gametocytes are stimulated to undergo gametogenesis and fertilization takes place within 10-20 minutes.

After 30 minutes in this solution at room temperature the cell suspension is layered on a single step Hypaque/Ficoll gradient (10 volumes Hypaque, 33.9% w/v in H$_2$O to 24 volumes Ficoll 400, 9% w/v in Hh$_2$O); Hypaque is made up from 50% sodium Hypaque (Winthrop Laboratory, NY). Ficoll 400 is from Pharmacia Fine Chemicals, Piscataway, NJ. Two volumes of the cell suspension are layered over 1 volume of gradient and spun for 10 minutes at 10,000×g at 20° C. The material collected at the interface contains zygotes and female gametes, white cells and few RBCs. Most of the RBCs, infected and uninfected, are found in the pellet.

The material from the interface is washed once in SA solution, pH 7.4, and spun for 5 minutes at 500×g for each washing. The final pellet is resuspended in 10 ml of SA solution, pH 7.4, in a 15 ml plastic centrifuge tube and 200 µl of a 1 mg/ml wheat germ agglutinin (Sigma Chemical Co., St. Louis, MO) solution added. Agglutination of host cells and host cell membranes is allowed to take place with gentle horizontal rotation of the tube to aid flocculation. The tube is then placed upright and the agglutinated material allowed to settle (5-10 minutes). The supernatant is passed through a Pasteur pipette whose lower portion had been gently but firmly packed with 'glass wool' (Pyrex brand wool filtering fibers; Corning, Corning, NY) making a mechanical filter about 1 cm in height. The effluent is collected and washed up to five or six times in SA solution, pH 7.4, by spinning in 5 ml plastic serum tubes (Corning) on a bench top centrifuge in 1 ml volumes at 500×g for 30 s each.

At the end of these procedures preparations of zygotes and female gametes are obtained generally representing 10-30% of the female gametocytes present in the original blood and comprising between $1-3 \times 10^8$ cells. The preparation is more than 99% pure with respect to any other cellular material.

Preparation of Ookinetes

Ookinetes are prepared from preparations of zygotes and female gametes as described above by incubating them at 26° C. for 24 hours at a cellular concentration of $2 \times 10^7$ ml in 5 ml polyethylene serum tubes (Sarstedt) containing Medium 199 with 17 mM glucose, 12 mM NaHCO$_3$, 1 mM L-glutamine, 125 µg gentamycin/ml, 100 units penicillin/ml and 100 µg streptomycin/ml. Following maturation at 24 hours the ookinetes are separated from the unfertilized female gametes on a single step Hypaque/Ficoll gradient (10 volumes Hypaque, 50% w/v in H$_2$O to 24 volumes Ficoll 400, 9% w/v in H$_2$O; Hypaque from Winthrop Laboratory, NY; Ficoll 400 from Pharmacia Fine Chemicals; Piscataway, NJ). Following centrifugation for 10 minutes at 10,000×g at 10° C., the mature ookinetes are recovered from the bottom of the gradient >95% free of the unfertilized gametes which collect at the interface. The purified ookinetes are washed and resuspended in SA solution.

Biosynthetic Radiolabelling, Surface Radioiodination, Immunoprecipitation and SDS-PAGE of Zygotes and Ookinetes of *P. gallinaceum*

Zygotes and ookinetes of *P. gallinaceum* prepared as described above are biosynthetically labelled in culture with $^{35}$S-methionine, or tritiated mannose, or glucosamine, or surface radioiodinated as intact cells with $^{125}$I by the lactoperoxidase method, extracted with 1% Triton X-100 and immunoprecipitated with MAbs (described below) followed by separation by SDS-PAGE.

Production of MAbs

Hybridoma cell lines and MAbs are derived from a BALB/c mouse immunized with purified mature ookinetes of *P. gallinaceum* prepared as described above. The mouse is injected intraperitoneally (ip) with $1 \times 10^7$ ookinetes in 0.5 ml of PBS containing 0.167 opacity units of *Bordetella perfussie* (approximately 10 organisms), a second i.p. inoculation and an intravenous inoculation, both without adjuvant, are given 30 and 40 days, respectively, after the first inoculation. Four days after the final inoculation, fusions between spleen cells from the immunized mouse and plasmacytoma line NS1 are performed using 50% polyethylene glycol (m.w. 1000, Sigma Chemical Co., St. Louis, MO). The hybrid cells are grown in 2 ml/well of hypoxanthine-aminopterinthymidine selective Dulbecco's medium and supernatants screened for anti-ookinete antibody production by an indirect immunofluorescence assay using live intact ookinetes. Hybrid cell lines producing anti-ookinete antibodies are grown as ascites tumors in Pristan (2, 3, 6, 10-tetramethyl pentadecane; Aldrich Chemical Co., Milwaukee, WI)-primed BALB/c mice the ascites fluids collected, heat inactivated at 56° C. and further tested by immunoprecipitation from surface radio-iodinated or biosynthetically labelled ookinetes and for their effects on infectivity of the parasites to *A. aegypti* mosquitoes. Cell lines producing antibodies which mediate suppression of infectivity of the fertilized parasites to mosquitoes are re-introduced into culture, cloned by limit dilution, and antibodies from the cloned lines re-tested as described above. MAbs are used in the form of heat inactivated ascitic fluid.

EXAMPLE 1

Effect of Complement. The PBS dialysed ammonium sulfate precipitated MAbs from ascitic fluid were tested for their effect of the infectivity of gametocytes of *P. falciparum* (line 7G8) to *An. freeborni* mosquitoes. Following preliminary tests, two MAbs (IA3-B8 and IIC5B10 both isotype $\gamma 2a$ were identified which act synergistically to suppress infectivity of the parasites to mosquitoes. These two MAbs were subsequently tested in four replicate experiments conducted as two parallel series. In one series, human serum, heat inactivated at 56° C. for 30 minutes, was used (Table 1); in the other, fresh serum from human blood drawn and defibrinated on the day of the experiment was used as a source of active complement (C) (Table 2). In the absence of active complement (Table 1) suppression of infectivity by individual MAbs was relatively weak. When IIC5-B10 and IA3-B8 were combined, however, infectivity was consistently suppressed by about 99%. The suppression achieved by the mixed MAbs was thus clearly synergistic. Similar synergistic suppression of infectivity by IA3-B8 and IIC5-B10 was achieved when active C was present (Table 2). Under these conditions, however, IA3-B8 consistently suppressed infectivity by at least 90%, demonstrating a complement mediated effect by this MAb. PBS dialysed, ammonium sulphate precipitated antibodies from ascite fluids which fail to suppress infectivity in preliminary tests were included as simultaneous controls in each experiment.

EXAMPLE 2

Figure 2A:
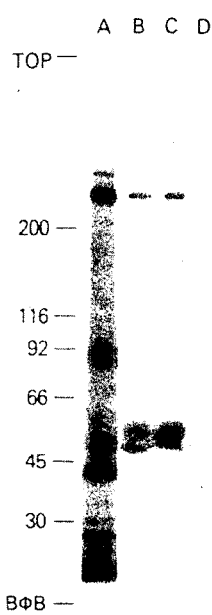
FIG. 2 depicts antigens precipitated from extracts of surface radioiodinated female gametes of *Plasmodium falciparum* by transmission-blocking monoclonal antibodies (MAbs) and separated by SDS-PAGE. (a) *P. falciparum* isolate BC1; SDS-PAGE under reducing conditions. Antigen extract (lane A); precipitated with IA3-B8 (lane B); with IIC5-B10 (lane C) and with ammonium-sulfate precipitated normal mouse serum (lane D). (b) *P. falciparum* line 7G8; SDS-PAGE under nonreducing conditions. Antigen extract (lane A); precipitated with IA3-B8 (lane B); with IIC5-B10 (lane C); with ammonium-sulfate precipitated normal mouse serum (lane D). (c) *P. falciparum* isolate BC1; SDS-PAGE under nonreducing conditions. Antigen extract (lane A); precipitated with IA3-B8 (lane B); with IIC5-B10 (lane C). Molecular weights are indicated in kilodaltons.

Extracts of $^{125}$I surface labeled female gametes of *P. falciparum* were immunoprecipitated with IIC5-B10 or IA3-B8 and separated on SDS-PAGE. The same three proteins were precipitated from gametes of an African isolate, BC1, by both MAbs and have apparent molecular weights under reducing conditions of 25, 59, and 53 kilodaltons (FIG. 2a, Lanes B and C).

TABLE 1

The Effect of Monoclonal Antibodies on the Infectivity to *Anopheles freeborni* Mosquitoes of Gametocytes of *Plasmodium falciparum* Grown in Culture Complement Inactivated

| Experiment Number | Monoclonal Antibodies | | | | SA Solution |
|---|---|---|---|---|---|
| | IIC5-B10 | IA3-B8 | IIC5-B10 + IA3-B8 | Other* | |
| 1 | 2.8 (20) | 5.3 (9) | 0.3 (12) | 24.8 (9) | 13.3 (19) |
| 2 | 0.1 (7) | 1.0 (12) | 0.0 (12) | 1.5 (12) | 0.7 (11) |
| 3 | 17.3 (12) | 5.4 (8) | 0.1 (10) | 46.6 (10) | 24.0 (16) |
| 4 | 3.0 (6) | 8.2 (6) | 0.0 (15) | 1.1 (14) | 6.0 (12) |
| Mean no. of oocysts per gut | 6.3 (45) | 4.3 (35) | 0.1 (49) | 16.0 (45) | 12.4 (58) |

Infectivity is expressed as the mean number of oocysts (products of parasite fertilization) per mosquito. Four replicate experiments are represented; the number of mosquitoes examined is indicated in parenthesis after the value for infectivity.
*"Other" represents infectivity in the presence of MAbs found to be without suppressive effect on infectivity in preliminary tests.
The human serum in the experiments represented here is heat inactivated before use.

TABLE 2

The Effect of Monoclonal Antibodies on the Infectivity to *Anopheles freeborni* Mosquitoes of Gametocytes of *Plasmodium falciparum* Grown in Culture Active Complement Present

| Experiment Number | Monoclonal Antibodies | | | | SA Solution |
|---|---|---|---|---|---|
| | IIC5-B10 | IA3-B8 | IIC5-B10 + IA3-B8 | Other | |
| 1 | 0.1 (10) | 0.2 (10) | 0.0 (10) | 7.2 (10) | 9.0 (20) |
| 2 | 0.1 (12) | 0.1 (12) | 0.0 (12) | 2.5 (12) | 4.0 (14) |
| 3 | 25.3 (11) | 2.0 (8) | 0.1 (18) | 48.9 (14) | 32.5 (28) |
| 4 | 2.1 (8) | 0.9 (17) | 0.3 (14) | 8.1 (7) | 6.4 (12) |
| Mean no. of oocysts per gut | 7.2 (41) | 0.7 (47) | 0.1 (54) | 19.6 (43) | 16.5 (74) |

The four replicate experiments represented are each run simultaneously with the corresponding experimental replicate in Table 1. In these experiments, however, the human serum used in the membrane feeding is freshly drawn and in its native state (i.e., complement systems intact). The results are expressed as in Table 1.

Figure 2B:
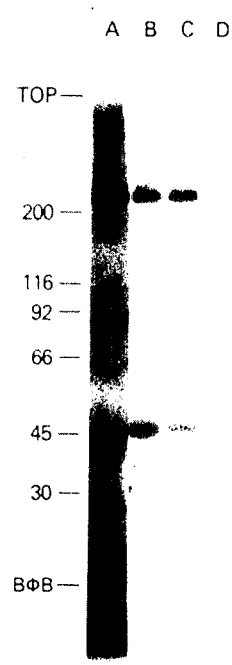
Figure 2C:
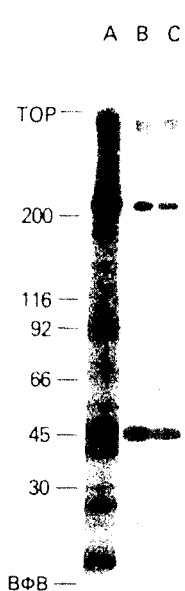

None of the labeled proteins were immuno-precipitated by ammonium sulfate precipitated normal mouse serum (Lane D). Equivalent proteins were precipitated from a Brazilian isolate 7G8 by IA3-B8 and IIC5-B10 (FIG. 2b, Lanes B and C). Resolution of the proteins of 59 and 53 kilodaltons in the immune precipitates was obscured by the presence of the heavy chain of mouse immunoglobulin in the same region of the gel. Under non-reducing conditions the immunoglobulins migrate higher up the gel and the gamete proteins were resolved in the immunoprecipitates (FIGS. 2b and c, Lanes B and C). Under these conditions, the apparent molecular weight of the three precipitated proteins changed to 235, 49, and 46 Kilodalton respeciively.

Both IIC5-B10 and IA3-B8 react by IF with air dried male gametes of *P. falciparum* demonstrating the presence of the target antigens on male as well as female gametes of the parasite. Neither MAb precipitated labeled material from surface-radioiodinated human erythrocytes; nor did they precipitate labeled material from gametes of *P. gallinaceum* or react with them by IF on live gametes.

EXAMPLE 3

The three proteins identified on the surface of gametes of *P. falciparum* isolate 7G8 by the MAbs IIC5-B10 and IA3-B8 were synthesized by gametocytes of this parasite. This was shown when cultured gametocytes of 7G8 were biosynthetically labelled with $^{35}$S-methionine, extracted with Triton X-100, and precipitated with the MAbs. Proteins of 255, 59, and 53 kilodalton were precipitated from this material by both IIC5-B10 and IA3-B8. These proteins were not biosynthetically labelled in cultures of asexual stages of the parasites; labelled material corresponding to these proteins could not be precipitated by IIC5-B10 or IA3-B8 from Triton X-100 extracts of such material.

EXAMPLE 4

Assay for Effect of MAbs on Infectivity of Fertilized Zygotes of *P. gallinaceum* to Mosquitoes. The effects of antibodies on infectivity of the parasites to mosquitoes were tested as follows. Blood from chickens with a 10 to 15% parasitemia of *P. gallinaceum* was drawn in a heparinized syringe and washed in 10 volumes of SA solution. The parasitized blood was resuspended from SA solution into four original blood volumes of a solution at 22° C. containing 8 mM Tris, 150 mM NaCl, 8 mM glucose, 25 mM NaHCO$_3$ and supplemented with 10% NCS (heat inactivated) at final pH 8.0. Gametogenesis was immediately stimulated under these conditions and fertilization was largely completed within 30 minutes. The fertilized blood was thereafter resuspended to its original hematocrit in appropriate dilutions of heat inactivated ascitic fluid containing MAb.

The suspension of fertilized parasites in ascitic fluid was fed in 200 μl amounts to cages of 20 female *Aedes aegypti* mosquitoes (starved for 24 hours) Swiss nylon monofilament screen (Pore size, 183 μm; Talko, Elmsport, NY) warmed to 40° C. through a glass water jacket. The mosquitoes were allowed to feed for 10 minutes; after discarding those which did not feed, the remainder were maintained for 7 days on sugar water in a 26° C. humidified room. The mosquitoes were then dissected and their midguts examined for the presence of oocysts. The number of oocysts (products or fertilization) per midgut was used as the measure of infectivity. Control batches of mosquitoes were treated in exactly the same way as the corresponding experimental batches, except that NCS (heat inactivated) was used to replace ascitic fluid.

For each MAb tested, the geometric mean number of oocysts per midgut was calculated and expressed as a percentage of that found in simultaneous controls.

One MAb, IID2-C5, suppressed the infectivity of fertilized zygotes of *P. gallinaceum* to *Aedes aegypti* mosquitoes by 90 to 99% below control levels. This MAb immunoprecipitated a protein of about 25 K from ookinetes of *P. gallinaceum* surface labelled with $^{125}$I. This protein was biosynthetically labelled by incubating zygotes with $^{35}$S-methionine as early as 3 hours after fertilization, as was shown by its precipitation by IID2-C5. The target antigen of this MAb which suppressed development of the fertilized zygote in mosquitoes was thus expressed within 3 hours of fertilization of the parasites. This molecule is a glycoprotein as shown by the fact that it may be biosynthetically labelled with glucosamine and mannose.

DEFINITIONS

Epitope—A structural component of an antigen molecule known to function as an antigenic determinant by allowing the attachment of certain antibody molecules.

Erythrocyte—The mature hemoglobin containing cell of vertebrate blood; non-nucleated in mammals, the equivalent cell is nucleated in birds.

Schizonts—A stage in the asexual life cycle of Plasmodium, covering the period from beginning of division of nuclear material until formation of mature merozoites.

Merozoites—The form of the malaria parasite invasive of erythrocytes and resulting from the splitting up of the schizont.

Gametocyte—The cell which by division produces gametes.

Gamete—Male or female reproductive cell.

Zygote—Organism produced by the union of two gametes.

Ookinete—Elongated, motile zygote of the malaria parasite as it bores through the epithelial lining of a mosquito's intestine, in the wall of which it becomes an oocyst.

We claim:

1. A process for blocking transmission of malaria parasites comprising providing anti-parasitic monoclonal antibodies IIC5-B10 and IA-3-B8 which specifically bind to an antigen on the surface of extracellular gametes of said malaria parasites, and feeding said monoclonal antibodies to mosquitoes in a blood meal containing gametocytes of the malaria parasites.

2. The process of claim 1 wherein the antigen on the surface of extracellular gametes of the malaria parasite comprises three proteins with molecular weights of 230–260 kilodaltons, 55–60 kilodaltons and 50–55 kilodaltons.

3. The process of claim 2 in which the malaria parasite is *Plasmodium falciparum*.

4. The process of claim 1 wherein additionally complement is combined with the anti-parasitic monoclonal antibodies and the combination is fed to mosquitoes during a blood meal.

5. The process of claim 1 wherein said monoclonal antibodies are a mixture of IIC5-B10 and IA-3-B8 monoclonal antibodies.

6. A process for blocking transmission of malaria parasites comprising providing anti-parasitic monoclonal antibody IID2-C5-1 which specifically binds to a glycoprotein expressed on the surface of the malaria parasite zygote three hours after fertilization, said glycoprotein having a molecular weight of 24–30 kilodaltons, and feeding said monoclonal antibody to mosquitoes in a blood meal containing gametocytes of the malaria parasites.

7. The process of claim 6 in which the malaria parasite is *Plasmodium gallinaceum*.

8. The process of claim 6 wherein additionally complement is combined with said monoclonal antibody and the combination is fed to the mosquitoes.

9. A process for blocking transmission of malaria parasites comprising providing monoclonal antibody IID2-C5-1, IIC5-B10-1 and IA-3-B8-5 which specifically bind the surface antigens of a malaria parasite; and feeding to mosquitoes malaria parasites and at least one of said monoclonal antibodies combined to form a blood meal.

10. A hybridoma secreting monoclonal antibody IIC5-B10-1 deposited in American type Culture Collection, accession #HB-8392.

11. A hybridoma secreting monoclonal antibody IA3-B8-5 deposited in American Type Culture Collection, accession #HB-8393.

12. A hybridoma secreting monoclonal antibody IID2-C5-1 deposited in American Type Culture Collection, accession #HB-8391.

* * * * *